(12) United States Patent
Silvis et al.

(10) Patent No.: US 9,297,726 B2
(45) Date of Patent: Mar. 29, 2016

(54) EXHAUST SAMPLING SYSTEM AND METHOD FOR WATER VAPOR MANAGEMENT

(75) Inventors: William Martin Silvis, Ann Arbor, MI (US); James Williamson, Pinckney, MI (US); Gerald Marek, Pinckney, MI (US); Douglas Edward Miller, Jr., Britton, MI (US)

(73) Assignee: AVL TEST SYSTEMS, INC., Plymouth, MI (US)

( * ) Notice: Subject to any disclaimer, the term of this patent is extended or adjusted under 35 U.S.C. 154(b) by 836 days.

(21) Appl. No.: 13/478,170

(22) Filed: May 23, 2012

(65) Prior Publication Data

US 2013/0317757 A1  Nov. 28, 2013

(51) Int. Cl.
   *G01N 1/22* (2006.01)

(52) U.S. Cl.
   CPC ............ *G01N 1/2247* (2013.01); *G01N 1/2252* (2013.01); *G01N 1/22* (2013.01); *G01N 2001/2261* (2013.01); *G01N 2001/2264* (2013.01)

(58) Field of Classification Search
   CPC ..... G01N 1/00; G01N 2203/00; B01D 45/00; G01M 1/00
   USPC .......... 73/23.2, 23.31, 53.01, 114.69, 114.71; 422/83
   See application file for complete search history.

(56) References Cited

U.S. PATENT DOCUMENTS

| | | | |
|---|---|---|---|
| 3,499,717 A * | 3/1970 | Well et al. ......................... 431/2 |
| 3,603,155 A | 9/1971 | Morris et al. | |
| 3,610,047 A | 10/1971 | List et al. | |
| 3,699,814 A | 10/1972 | Kaufman | |
| 3,793,887 A | 2/1974 | Anderson et al. | |
| 4,040,783 A | 8/1977 | Collin | |
| 5,058,440 A | 10/1991 | Graze, Jr. | |
| 5,195,318 A | 3/1993 | Shinzawa et al. | |
| 5,456,124 A | 10/1995 | Colvin | |
| 5,546,788 A | 8/1996 | Dickow | |
| 5,650,565 A | 7/1997 | Nagy et al. | |

(Continued)

FOREIGN PATENT DOCUMENTS

| | | |
|---|---|---|
| DE | 4017473 A1 | 11/1991 |
| EP | 42800 | 12/1981 |

(Continued)

OTHER PUBLICATIONS

Edkins, Jo; Mean, median, mode; 2006; Numbers Index, http://gwydir.demon.co.uk/jo/numbers/pictogram/box.htm, pp. 1-3.*

(Continued)

*Primary Examiner* — Gregory J Toatley
*Assistant Examiner* — Christine Liao
(74) *Attorney, Agent, or Firm* — Harness, Dickey & Pierce, P.L.C.

(57) ABSTRACT

Disclosed is an exhaust sampling system including a plurality of exhaust sampling system zones. The zones are, at least, a sampling conduit, a fill circuit, and a read circuit. A controller is programmed to predict a minimum dilution ratio to avoid condensation in one of the exhaust sampling system zones. The controller is further programmed to run a test procedure in which a sample of exhaust is diluted with a make-up gas at a selected minimum dilution ratio that is greater than or equal to the predicted minimum dilution ratio. Further disclosed are methods of predicting whether condensation occurs during a test procedure.

14 Claims, 7 Drawing Sheets

(56) References Cited

U.S. PATENT DOCUMENTS

| | | | |
|---|---|---|---|
| 5,821,435 A | 10/1998 | Kojima | |
| 6,016,711 A | 1/2000 | Ullman et al. | |
| 6,134,942 A | 10/2000 | Pasquereau et al. | |
| 6,282,944 B1 | 9/2001 | Bornemann | |
| 6,370,936 B1 | 4/2002 | Yamagishi et al. | |
| 6,405,577 B2 | 6/2002 | Hanashiro et al. | |
| 6,412,333 B2 | 7/2002 | Inoue et al. | |
| 6,443,021 B2 | 9/2002 | Hanashiro et al. | |
| 6,470,732 B1 | 10/2002 | Breton | |
| 6,490,937 B2 | 12/2002 | Hanashiro et al. | |
| 6,497,156 B2 | 12/2002 | Dageforder | |
| 6,578,440 B2 | 6/2003 | Lewis | |
| 6,962,090 B2 | 11/2005 | McDonald et al. | |
| 7,071,002 B1* | 7/2006 | Tefft et al. | 436/137 |
| 7,559,262 B2 | 7/2009 | Silvis et al. | |
| 8,181,543 B2 | 5/2012 | Silvis et al. | |
| 8,272,248 B2 | 9/2012 | Guenther et al. | |
| 2001/0003915 A1 | 6/2001 | Inoue et al. | |
| 2001/0013245 A1* | 8/2001 | Hanashiro et al. | 73/23.31 |
| 2003/0093943 A1 | 5/2003 | Jordan | |
| 2003/0149536 A1 | 8/2003 | Silvis et al. | |
| 2004/0139785 A1 | 7/2004 | Abdul-Khalek | |
| 2004/0200265 A1* | 10/2004 | Eden et al. | 73/23.31 |
| 2004/0226354 A1* | 11/2004 | Schmidt | 73/118.1 |
| 2005/0056103 A1 | 3/2005 | Hirai et al. | |
| 2005/0109128 A1 | 5/2005 | Pasquereau et al. | |
| 2005/0160838 A1 | 7/2005 | Weaver | |
| 2005/0236040 A1* | 10/2005 | Farthing et al. | 137/93 |
| 2006/0243026 A1 | 11/2006 | Graze et al. | |
| 2010/0000339 A1* | 1/2010 | Silvis et al. | 73/863.01 |
| 2011/0146378 A1* | 6/2011 | Brand et al. | 73/23.31 |
| 2011/0252864 A1 | 10/2011 | Guenther et al. | |
| 2012/0304737 A1 | 12/2012 | Guenther et al. | |

FOREIGN PATENT DOCUMENTS

| | | | |
|---|---|---|---|
| EP | 610523 | A1 | 8/1994 |
| EP | 928962 | A1 | 7/1999 |
| EP | 973080 | A2 | 1/2000 |
| EP | 2469259 | A1 | 6/2012 |
| JP | 07-035660 | | 2/1995 |
| JP | 07035660 | | 5/1995 |
| JP | 8226879 | | 9/1996 |
| JP | 10318810 | | 12/1998 |
| JP | H10-318810 | A | 12/1998 |
| JP | 11108809 | | 4/1999 |
| JP | 11344425 | | 12/1999 |
| JP | H11-344425 | A | 12/1999 |
| JP | 2000180315 | | 6/2000 |
| JP | 2000180315 | A | 6/2000 |
| JP | 2000292321 | A | 10/2000 |
| JP | 2001004504 | | 1/2001 |
| JP | 2005055333 | | 3/2005 |
| JP | 2006105024 | | 4/2006 |
| JP | 2006105024 | A | 4/2006 |
| WO | 0014506 | A1 | 3/2000 |
| WO | 0190741 | A2 | 11/2001 |
| WO | 2013181145 | A1 | 12/2013 |

OTHER PUBLICATIONS e-CFR Title 40, Part 1065, Engine-Testing Procedures, 164 pages.
e-CFR Title 40, Part 1066, Vehicle-Testing Procedures, 73 pages.
Nevius et al., "Improved PHEV Emission Measurements in a Chassis Dynamometer Test Cell," SAE International J. Engines, vol. 3, Issue 1, Apr. 12, 2010, pp. 1113-1123.
Hood et al., "Predicting and Preventing Water Condensation in Sampled Vehicle Exhaust for Optimal CVS Dilution," SAE Technical Paper 980404, 1998, doi:10.4271/980404.
"40 CFR 1065—Engine-Testing Procedures," http://www.law.cornell.edu/cfr/text/40/1065, Apr. 3, 2012.
"Electronic Code of Federal Regulations, Title 40: Protection of Environment." http://ecfr.gpoaccess.gov, Apr. 3, 2012.
International Search Report and Written Opinion of the International Searching Authority for PCT/US2013/042871, mailed Sep. 5, 2013; ISA/KR.

* cited by examiner

EXHAUST SAMPLING SYSTEM AND METHOD FOR WATER VAPOR MANAGEMENT

BACKGROUND

In typical exhaust sampling systems, such as constant volume samplers (CVS), engine exhaust is diluted with a make-up gas, or diluent, and a sample of the diluted exhaust is proportionally extracted and stored in one or more sample bags. Depending upon the engine size, drive cycle and ambient conditions, the CVS total flow rate, which includes both the make-up gas and engine exhaust, is selected to ensure the diluted exhaust sample does not condense water when stored in the bags.

In addition to determining an appropriate CVS total flow rate, some systems fill the sample bags with a gas, such as a pre-fill gas, to avoid bag condensation. Some other systems apply heat to the sample bags such that the temperature of the sample is maintained above the dew point.

SUMMARY

Disclosed is an exhaust sampling system including a plurality of exhaust sampling system zones. The zones are, at least, a sampling conduit, a fill circuit, and a read circuit. A controller is programmed to predict a minimum dilution ratio to avoid condensation in one of the exhaust sampling system zones. The controller is further programmed to run a test procedure in which a sample of exhaust is diluted with a make-up gas at a selected minimum dilution ratio that is greater than or equal to the predicted minimum dilution ratio. Further disclosed are methods of predicting whether condensation occurs during a test procedure.

These and other features of the present disclosure can be best understood from the following drawings and detailed description.

BRIEF DESCRIPTION OF THE DRAWINGS

The drawings can be briefly described as follows.

DETAILED DESCRIPTION

Figure 1:
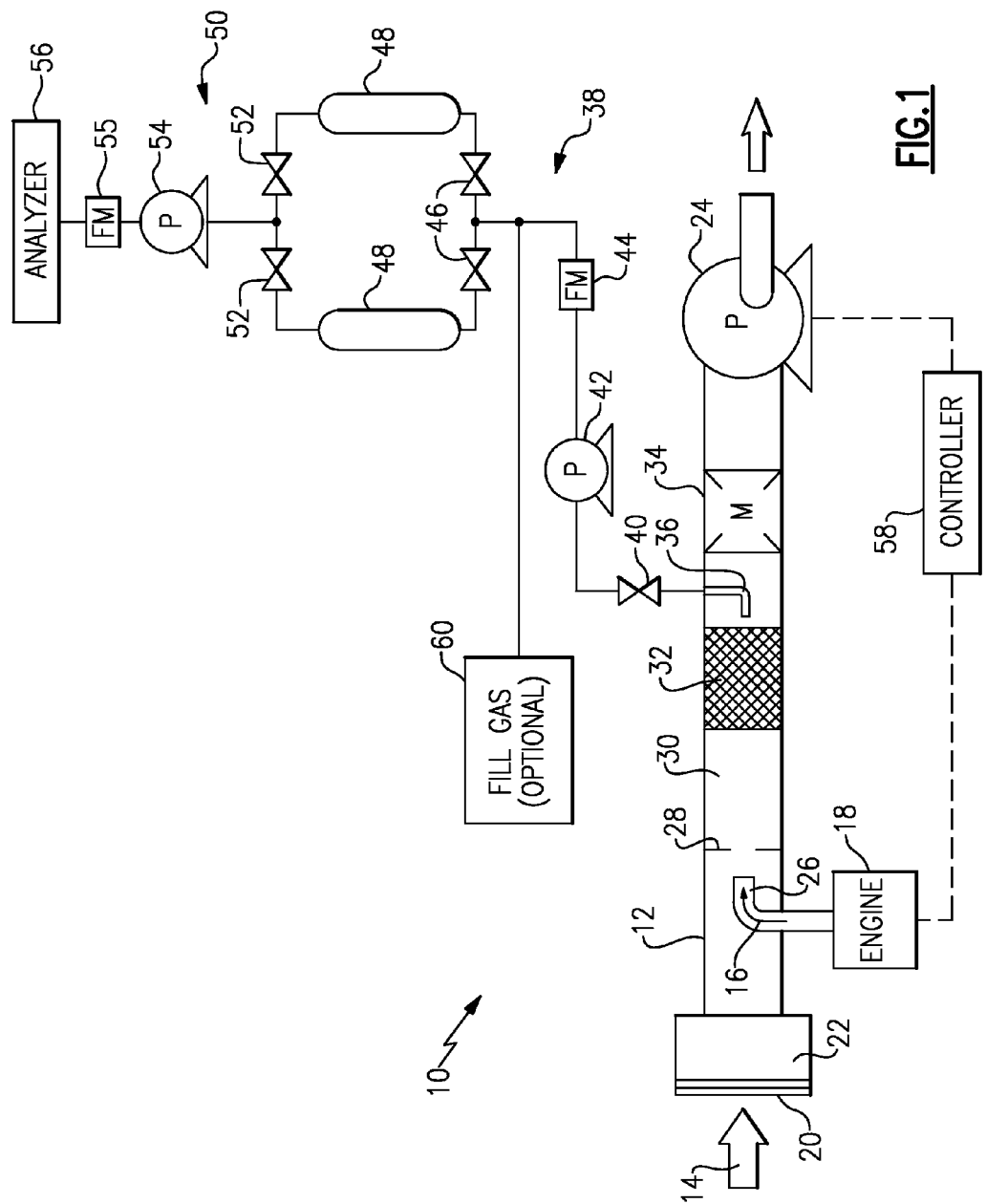
FIG. 1 is a schematic view of an example exhaust sampling system.

A schematic view of an example exhaust sampling system 10 is shown in FIG. 1. In particular, the illustrated system 10 is a CVS. An example CVS is present in U.S. Pat. No. 7,559,262, the entirety of which is herein incorporated by reference. It should be understood, however, that this application extends to other types of exhaust sampling systems, and is not limited to the particularities of the illustrated system 10.

The example system 10 includes a sampling conduit 12 configured to receive a make-up air 14 and exhaust 16 from an engine 18. The make-up air 14 is directed to the sampling conduit 12 by way of an inlet 20 formed in one end of the sampling conduit. The inlet 20 is provided with a filter 22 in this example. A pump 24 is positioned opposite the inlet 20 to draw a desired amount of make-up air into the sampling conduit 12. Exhaust 16 is directed into the sampling conduit 12 by way of a tail pipe 26.

As used herein, the term exhaust refers to the various fluids emitted from an engine (including gasses and vapors), as well as the particulate matter (PM) suspended therein. PM is commonly emitted from engines and typically includes carbonaceous matter in elemental form (or, soot) and carbonaceous matter in the form of volatile and semi-volatile hydrocarbon compounds (which may be SOF, or soluble organic fraction), and other organic and inorganic compounds (such as sulfates). The make-up air discussed above can be any type of diluent, such as ambient air, whose water concentration is known or readily determinable.

As illustrated, the sampling conduit 12 further includes a mixer 28, a tunnel 30, a heat exchanger 32, and a measuring device 34. A detailed discussion of these components is present in U.S. Pat. No. 7,559,262. While the sampling conduit includes these components 28, 30, 32, 34 in this example, this application extends to other types of sampling conduits, including conduits without these components.

Downstream of the inlet 20 and the tail pipe 26 is a sampler 36 for extracting a sample of the mixture of the makeup gas 14 and the exhaust 16. The mixture of the makeup gas 14 and the exhaust 16 is referred to herein as the diluted exhaust. The sample, sampled by sampler 36, is referred to as the diluted exhaust sample.

Downstream of the sampler 36, the diluted exhaust sample is directed through a fill circuit 38. In this example, the fill circuit includes a valve 40, pump 42, and a flow meter 44. The fill circuit 38 further includes independently adjustable valves 46 leading to a respective sample bag 48. While the fill circuit 38 is shown including the valve 40, pump 42 and flow meter 44, the fill circuit could include any combination of components, as desired. As used herein, use of the term fill circuit 38 refers to the portion of the sampling system 10 downstream of the sampling conduit 12 and upstream of the sample bags 48. The term fill circuit can be inclusive of the sampler 36, in some examples.

As illustrated, the fill circuit 38 directs the diluted exhaust sample to two sample bags 48, however this application extends to disclosures which include any number of bags, including only one sample bag. Depending on the number of sample bags 48, the number of valves 46 can be adjusted accordingly.

Downstream of the bags 48 is a read circuit 50, which includes independently adjustable valves 52, a pump 54, a flow meter 55, and an emissions analyzer 56, which may be a bench-type analysis unit. Like the fill circuit 38, the read circuit 50 may include any combination of desired components. As used herein, the term read circuit 50 refers to the portion of the sampling system 10 downstream of the bags 48.

A controller 58, which may be any type of known computer including a computer readable medium with the capability of storing instructions executable by the controller. The controller 58 is further in communication with each of the disclosed system components. For example, the controller is operable to control and monitor the engine 18, and is further capable of independently operating the various pumps 24, 42, 54 and valves 40, 46, 52.

Variations of the system 10 come within the scope of this disclosure. For example, in one variation the system 10 fills the sample bags 48 with a gas, such as a pre-fill gas from a source 60, before filling the bags with the diluted exhaust sample to ensure an accurate measurement at the analyzer 56. Such a system is disclosed in U.S. Pat. No. 7,559,262. This disclosure extends to systems that do not include a pre-filling feature. This disclosure further extends to systems that include a post-filling feature either alone, or in combination with, a pre-filling feature.

Figure 2:
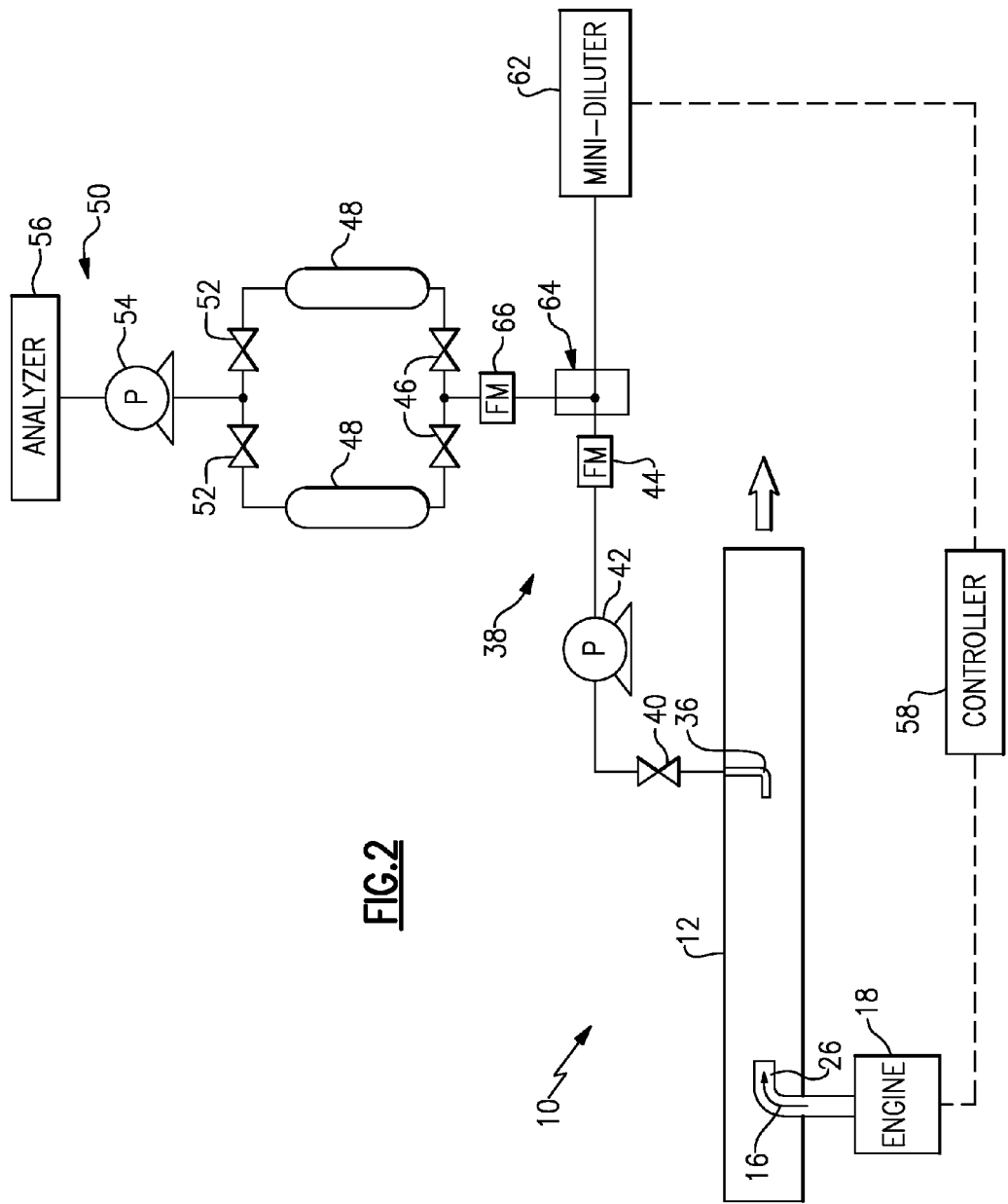
FIG. 2 is a schematic view of another example exhaust sampling system.

In another example, the system 10 includes a mini-diluter 62, such as the one illustrated in FIG. 2. Between FIGS. 1 and 2, like reference numerals are used to indicate like elements. In FIG. 2 the exhaust 16 from the engine 18 is directed into the sampling conduit 12 and is sampled by the sampler 36. The exhaust sample is diluted with a make-up gas from the mini-diluter 62, at the mixer 64. An example system including a mini-diluter is U.S. Patent Application Publication No. 2010/0000339, the entirety of which is herein incorporated by reference.

With reference back to FIG. 1, an exemplary emissions test procedure is conducted by directing exhaust 16 from the engine 18 into the sampling conduit 12, and diluting the exhaust 16 with the make-up air 14 at a minimum dilution ratio, $DR_{CVS-MIN}$, selected in advance of the procedure, as explained below. To dilute the exhaust 16 at the selected minimum dilution ratio, the controller 58 is programmed to instruct the pump 24 to draw an appropriate amount of make-up air 14 into the sampling conduit. In the example of FIG. 2, dilution would take place at the mixer 64, by way of instructions from the controller 58 to the mini-diluter 62.

The diluted exhaust sample is directed from the sampling conduit 12 to the sample bags 48, by way of the fill circuit 38. The diluted exhaust sample is collected in the sample bags 48 during the test procedure. Following the test procedure, the diluted exhaust sample is directed from sample bags 48 downstream to the read circuit 50, and ultimately to an analyzer 56.

During test procedures such as the example procedure described above, the formation of condensation in the diluted exhaust sample not only leads to inaccurate test results, but certain legislation prohibits condensation from being permitted inside the sample bags. New legislation is even more restrictive, and prohibits condensation from forming in more than just the sample bags 48. In other words, if condensation occurs at any point in the sampling system 10 during a test procedure, the new legislation effectively renders that test procedure compromised, and a new test procedure would be required.

Accordingly, this disclosure considers not only the sample bags 48, but alternatively, or in addition, considers at least one of the read circuit 38, the fill circuit 50, and the sampling conduit 12, when selecting a minimum dilution ratio $DR_{CVS-MIN}$ for the exhaust 16.

In general, the dilution ratio $DR_{CVS}$ is defined in accordance with the following:

$$DR_{CVS} = \frac{Q_m + Q_{ex}}{Q_{ex}}$$

where $Q_m$ is the make-up gas 14 flow rate and $Q_{ex}$ is an exhaust 16 flow rate. Once $DR_{CVS-MIN}$ is selected (e.g., $DR_{CVS}$ is set to $DR_{CVS-MIN}$), as discussed below, then the flow rate in the sampling conduit $Q_{CVS}$ is provided in accordance with:

$$Q_{CVS} = DR_{CVS-MIN} \cdot Q_{ex-ave}$$

where $Q_{ex-ave}$ is an average expected exhaust 16 flow rate during a test procedure. Alternatively, $Q_{ex-ave}$ could be a running average of exhaust 16 flow rate during the procedure. Given $DR_{CVS-MIN}$, the controller 58 is operable to provide an appropriate $Q_{CVS}$.

As generally mentioned above, the problem of condensation could be avoided by excessively diluting the exhaust 16 with the make-up gas 14. However, this would lead to an exhaust sample that would be extremely difficult to analyze, due to the high content of make-up gas 14 in the diluted exhaust sample. Accordingly, in one example of this disclosure the minimum dilution ratio $DR_{CVS-MIN}$ is selected such that it is as low as possible, while still being high enough to avoid condensation within the various components of the exhaust sampling system 10. To find this optimum $DR_{CVS-MIN}$, dilution ratios to avoid condensation in the fill circuit 38, the bags 48, the read circuit 50, and the sampling conduit 12 are separately determined, and the minimum dilution ratio of the exhaust 16 is set such that it is greater than or equal to a maximum of the predicted dilution ratios.

In particular, and with reference to FIG. 3, a minimum dilution ratio to avoid condensation in the fill circuit 38 $DR_{fill-min}$ is predicted at 68, and is defined as follows:

$$DR_{fill-min} \geq \frac{W_{ex-max}}{W_{fill-sat} - W_m}$$

where $W_{ex-max}$ is a maximum expected water concentration in the exhaust during the test procedure, $W_{fill-sat}$ is an expected saturated water concentration to be associated with the fill circuit 38 during the test procedure, and $W_m$ is an expected water concentration in the make-up gas during the test procedure. In one example, $W_{fill-sat}$ is determined from the following equation:

$$W_{fill-sat} = \frac{P_{H2O-vap}(T_{fill})}{P_{fill}}$$

where $P_{H2O-vap}$ is a saturation vapor pressure that is identified using a known method (for example, a look-up table). In another example, $P_{H2O-vap}$ is identified using certain federal regulations as a guide. In this example, the input temperature $T_{fill}$ is an expected average temperature of the diluted exhaust sample in the fill circuit 38 during a given test procedure. $P_{fill}$ is an expected average pressure of the diluted exhaust sample in the fill circuit 38 during the test procedure. $T_{fill}$ and $P_{fill}$ can be determined by considering ambient conditions, for example, as well as the $T_{fill}$ and $P_{fill}$ present during prior, similar tests. In one example, $T_{fill}$ is selected such that it is above the dew point of the mixture of the make-up gas 14 and the exhaust 16 at the minimum dilution ratio expected during testing, thus providing a built-in safety factor.

The remaining variables in the $DR_{fill-min}$ equation, $W_{ex-max}$ and $W_m$, are predicted based on inputs from the engine and the surrounding system. For example, the composition of the fuel combusted by the engine, as well as the properties and composition of the engine intake air will impact the water concentration in the exhaust, $W_{ex-max}$. In the example where the make-up gas 14 is ambient air, the water concentration in the make-up gas 14 is determined based on parameters such as the temperature and pressure of the surroundings of the system 10. Various pressure and temperature sensors can be positioned relative to the system 10, and these sensors are capable of communicating with the controller 58.

At 70, a minimum dilution ratio to avoid condensation in the read circuit, $DR_{read-min}$, is predicted. Similar to $DR_{fill-min}$, $DR_{read-min}$ is predicted in accordance with:

$$DR_{read-min} \geq \frac{W_{ex-ave} - W_m}{W_{read-sat} - W_m}$$

where $W_m$ is defined above, $W_{ex-ave}$ is an is a average expected water concentration in the exhaust during the test procedure, and $W_{read-sat}$ is an expected saturated water concentration to be associated with the read circuit 50 during the test procedure. $W_{read-sat}$ is determined in a manner similar to $W_{fill-sat}$, above, and is based on $T_{read}$ and $P_{read}$, an expected average temperature and pressure of the diluted exhaust sample in the read circuit 50 during a given test procedure. In particular, in the example, $T_{read}$ is set above the dew point that corresponds to the water content in the diluted exhaust sample, and $P_{read}$ is above a pressure to which the diluted exhaust sample is raised when pumping (e.g., with pump 54) to the analyzer 56.

Likewise, a predicted minimum dilution ratio is determined for the bags at 72. $DR_{bag-min}$ is predicted in accordance with:

$$DR_{bag-min} \geq \frac{W_{ex-ave} - W_m}{W_{bag-sat} - W_m}$$

where $W_{bag-sat}$ is an expected saturated water concentration to be associated with the at least one sample bag 48 during the test procedure. $W_{bag-sat}$ is determined in a manner similar to $W_{read-sat}$ and $W_{fill-sat}$, above, and is based on and $P_{bag}$, an expected average temperature and pressure of the diluted exhaust sample within the bags 48 during a test procedure. $T_{bag}$ will need to be above the dew point of the diluted exhaust sample in some examples. When computing $DR_{bag-min}$, some examples could substitute $W_{ex-ave}$ with a maximum integrated value for the concentration of water in the exhaust gas, to protect for peak exhaust. That is, while the actual $W_{ex-ave}$ could be used, some examples would substitute the value for $W_{ex-ave}$ with the average plus a test-dependent margin.

Further, a predicted minimum dilution ratio is determined for the sampling conduit 12, at 73. $DR_{tun-min}$ is predicted in accordance with:

$$DR_{samp-cond-min} \geq \frac{W_{ex-max} - W_m}{W_{tun-sat} - W_m}$$

where $W_{ex-max}$ and $W_m$ are defined above, and $W_{tun-sat}$ is an expected saturated water concentration to be associated with the sampling conduit 12 during the test procedure. $W_{samp-cond-sat}$ is determined in a manner similar to $W_{fill-sat}$, above, and is based on $T_{samp-cond}$ and $P_{samp-cond}$, an expected average temperature and pressure of the diluted exhaust sample in the sampling conduit 12 during a given test procedure. In particular, in the example, $T_{samp-cond}$ is set above the dew point that corresponds to the water content in the diluted exhaust sample, and $P_{samp-cond}$ is assumed to be equal to atmospheric pressure.

In one example, during the test, the actual temperature of bags $T_{bag}$ is higher by roughly 4-5° C. than the $T_{bag}$ used in the calculations, to give some safety factor. $P_{bag}$ may vary between the calculations and actual test conditions to provide a safety factor. Likewise, $DR_{fill-min}$ and $DR_{read-min}$ can be provided with built-in safety factors.

Once these minimum dilution ratios are predicted at steps 68, 70 and 72, the controller 58 selects an exhaust minimum dilution ratio, $DR_{CVS-MIN}$, that is greater than or equal to a maximum of the predicted minimum dilution ratios, $DR_{fill-min}$, $DR_{bag-min}$, $DR_{read-min}$, and $DR_{samp-cond-min}$. $DR_{CVS-MIN}$ is selected, at 74, as follows:

$$DR_{CVS-MIN} \geq \max(DR_{fill-min}, DR_{read-min}, DR_{bag-min}, DR_{samp-cond-min})$$

In one example test procedure, exhaust 16 is diluted with the make-up gas 14 at a ratio equal to $DR_{CVS-MIN}$. It is possible in some examples to dilute the exhaust at a ratio above the maximum of the predicted ratios for an added safety factor. However, as mentioned above, more accurate test results are possible with a lower dilution ratio. In one example, $DR_{CVS-MIN}$ is selected such that the make-up gas 14 is mixed with the exhaust 16 at a ratio within a range of 1:1 and 10:1.

The ratios $DR_{fill-min}$, $DR_{bag-min}$, $DR_{read-min}$, $DR_{samp-cond-min}$, and $DR_{CVS-MIN}$ are absolute minimums, such that the minimum dilution ratio should not drop below $DR_{CVS-MIN}$ at any point during the test procedure. In another example, the overall average dilution ratio over the course of a test would not drop below $DR_{CVS-MIN}$. In yet another example, the ratios are running averages, such that a running average of the dilution should not drop below $DR_{CVS-MIN}$.

Figure 4:
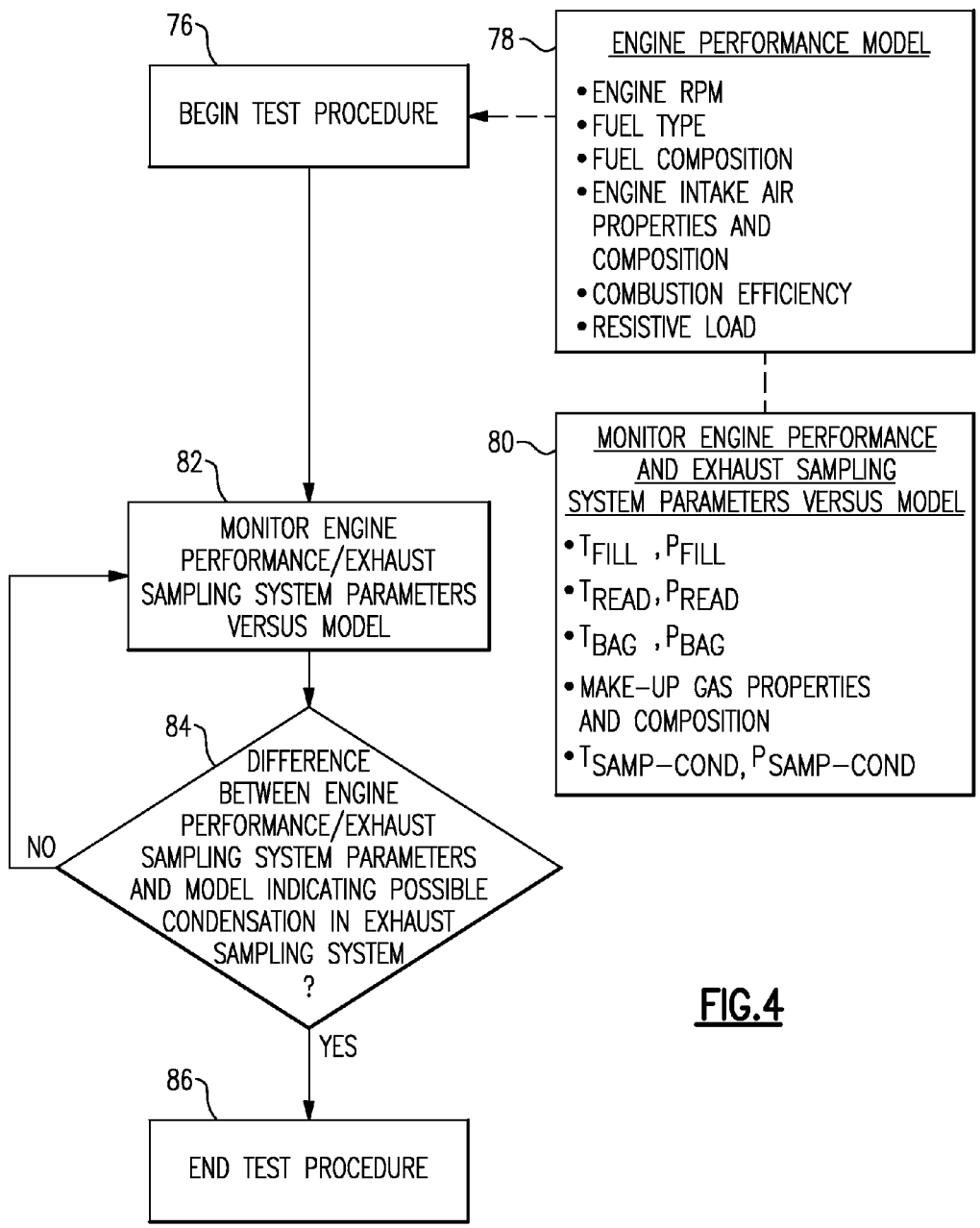
FIG. 4 is a flow chart illustrating example steps for determining whether a test procedure has been compromised.

In another example, the controller 58 dilutes the exhaust 18 at a ratio $DR_{CVS-MIN}$ determined based on at least one test parameter, which can include parameters from an engine or vehicle performance model 78 and parameters 80 of the system 10, as illustrated in FIG. 4. In this example, the engine performance model 78 is a known model associated with the particular type of engine involved in the test procedure. The at least one test parameter can further include coefficients from a dynamometer, such as settings for resistive load, which may relate to peak exhaust expected during a test cycle.

Regardless of how $DR_{CVS-MIN}$ is selected, average and maximum exhaust flow rate from the engine or vehicle over the course of the test procedure, $Q_{ex-ave}$ and $Q_{ex-max}$, can be estimated by given values, or, for example, can be predicted based on an estimated engine horsepower throughout the test procedure. Then the minimum $Q_{CVS-min}$ used throughout the test procedure can be provided as follows:

$$Q_{CVS-min} \geq \max(Q_{ex-max} \cdot DR_{fill-min}, Q_{ex-ave} \cdot DR_{read-min}, Q_{ex-max} \cdot DR_{bag-min}, Q_{ex-max} \cdot DR_{samp-cond-min})$$

In one example, the at least one test parameter includes such parameters as resistive load (e.g., dyno coefficients), engine RPM, fuel type, fuel composition, engine or vehicle intake air properties and composition, and combustion efficiency. Certain exhaust sampling system parameters would also be relevant in determining a minimum dilution ratio, as generally mentioned above, and would impact the engine performance model 78. These parameters 80 include $T_{fill}$ and $P_{fill}$, $T_{read}$ and $P_{read}$, $T_{bag}$ and $P_{bag}$, $T_{samp-cond}$ and $P_{samp-cond}$ and the composition properties of the make-up gas 14 (e.g., portions attributable to $N_2$, $O_2$, etc). For these parameters, a known engine performance model is determinable, and the controller can select a flow rate $Q_{CVS}$ for a required minimum dilution ratio $DR_{CVS-MIN}$.

Figure 3:
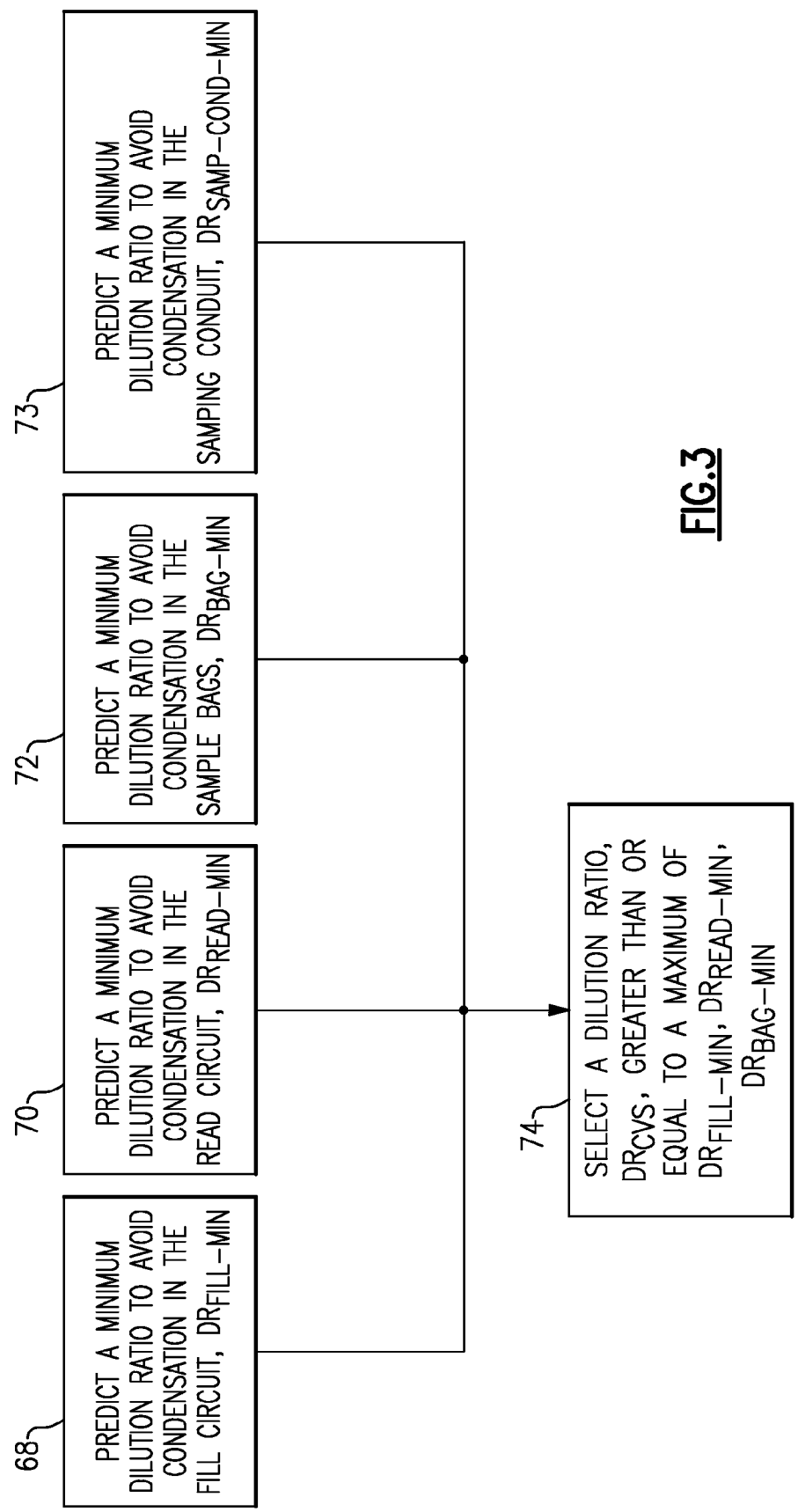
FIG. 3 is a flow chart illustrating example steps for selecting a minimum dilution ratio for a test procedure.

Alternatively, the minimum dilution ratio selected for the test of FIG. 4 could be determined based on the method of FIG. 3. Regardless of how $DR_{CVS}$ is selected, an emissions test procedure begins as illustrated at 76 in FIG. 4. As mentioned, the test procedure could dilute exhaust either at a minimum ratio selected in step 74, or at a minimum ratio determined based on at least one of the test parameters. In either case, once $DR_{CVS-MIN}$ is selected, the controller can suggest an optimized flow rate $Q_{CVS}$.

During the test, at 82, the controller 58 will monitor the actual performance of the test parameters relative to the model to determine whether the difference between the two indicates a possible condensation in the exhaust sampling system 10, at 84. If such an indication is present such that the tests may be compromised by potential condensation, the test procedure is ended at 86.

Figure 5:
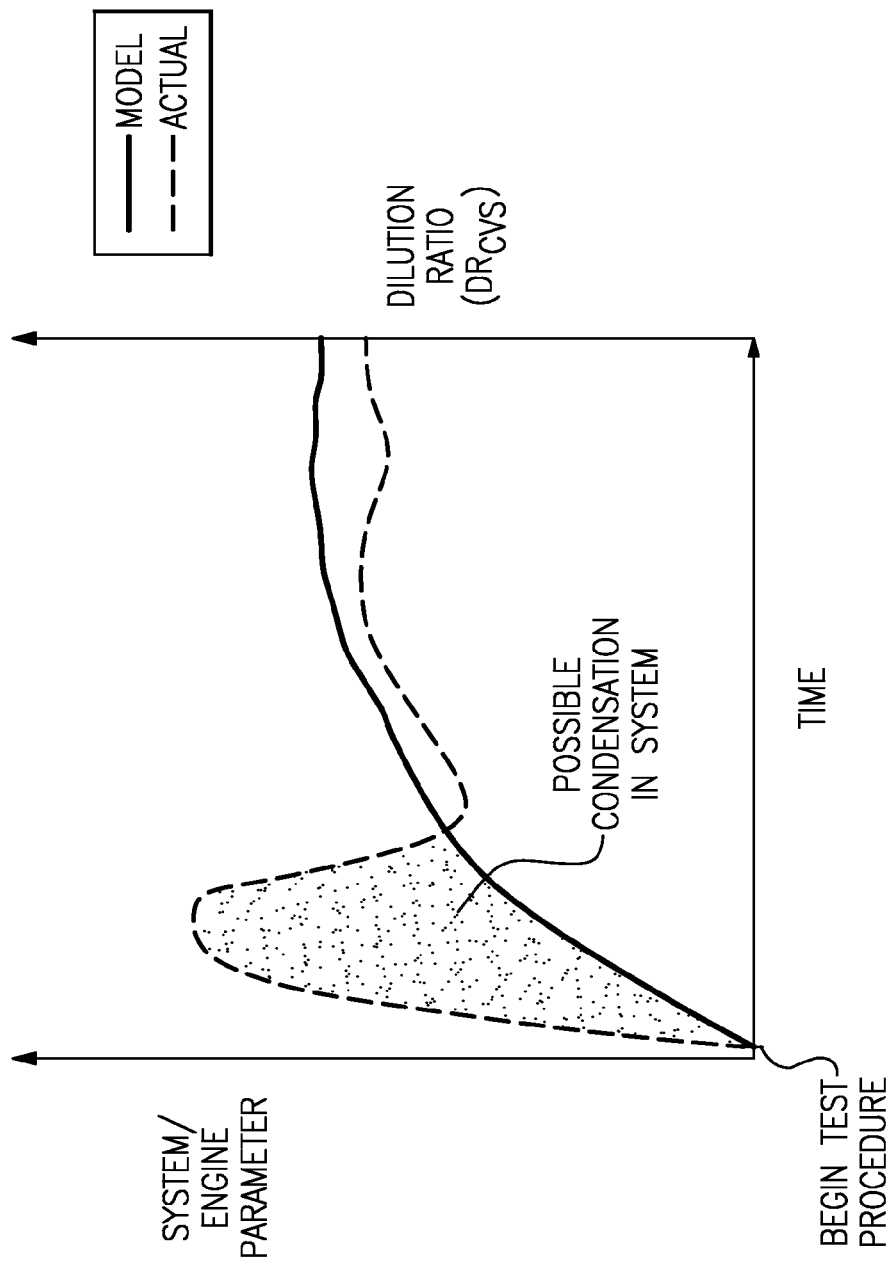
FIG. 5 is an example of the engine performance considered in the flow chart of FIG. 4.

A graphical representation of a scenario indicating a possible compromise in the test procedure is shown in FIG. 5. In the illustrated example, an engine 18 or system 10 parameters exceeds a value predicted by the model for an amount of time, as indicated by the shaded-in area between the actual value of the parameter and the value predicted by the model.

In one example, during the test procedure, the controller 58 monitors RPM of the engine 18 relative to a model relating engine RPM to minimum dilution ratio. If the engine RPM exceeds the value associated with the model such that the minimum dilution ratio $DR_{CVS-MIN}$ is not sufficient to avoid condensation, as represented in the shaded area of FIG. 5, the controller 58 ends the test. In another example, when ambient air is used as the make-up gas 14, the controller 58 monitors the relative humidity of the ambient air. An unexpected peak in the relative humidity can indicate a compromised test.

Figure 6:
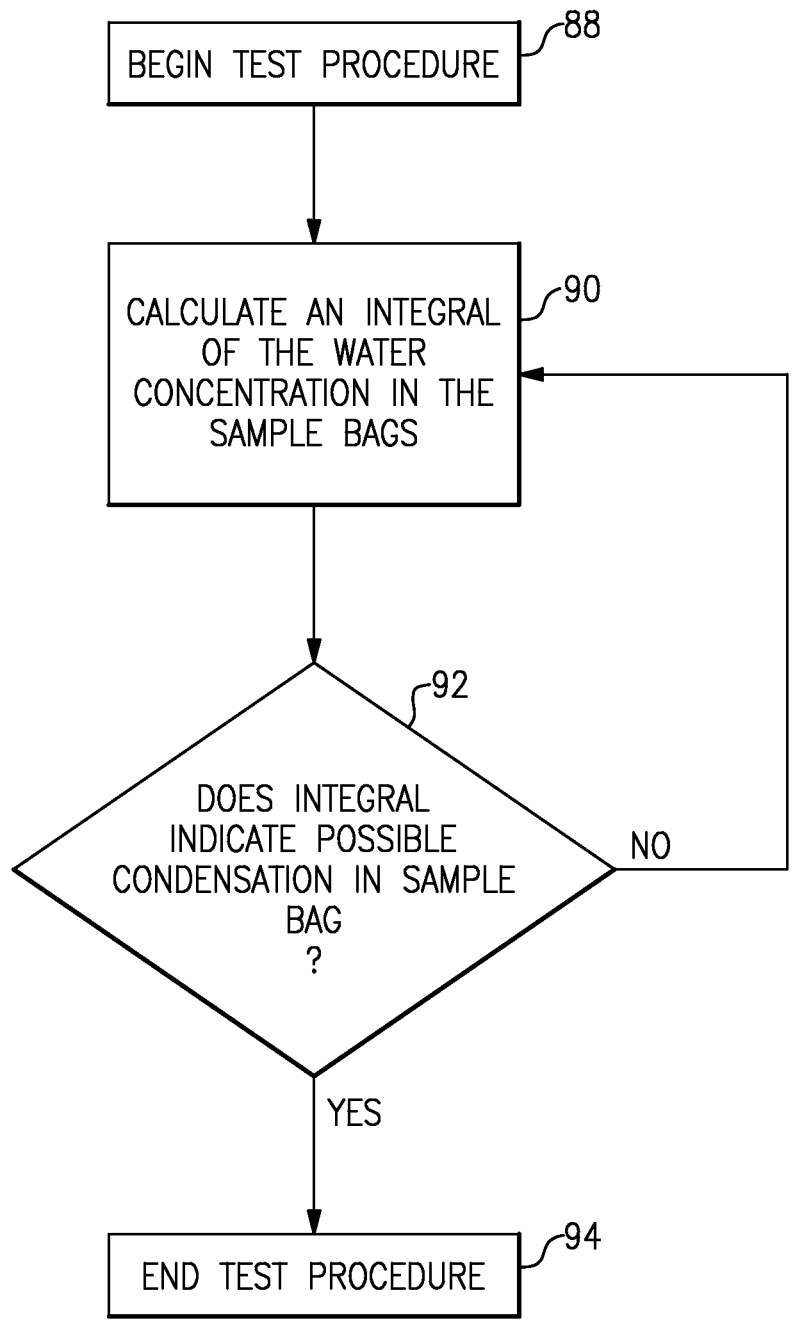
FIG. 6 is another flow chart illustrating example steps for determining whether a test has been compromised.

Another feature of this disclosure is represented in the flowchart of FIG. 6. During a test procedure, which begins at 88, an integral of the saturated water concentration within the sample bags, $W_{bag-sat-int}$, is calculated at 90. That is, $W_{bag-sat}$ is monitored as a function of time during the test procedure, and the integral of $W_{bag-sat}$ from time zero to "t" is used to determine whether there is concentration in bags at time "t." The integral is calculated at set intervals, for example (e.g., t is 1 second, 2 seconds, 3 seconds, etc). From this integral, $W_{bag-sat-int}$, the controller 58 determines, at 92, whether a possible condensation in the sample bags 48 is indicated, by comparing $W_{bag-sat-int}$ with a model, for example. If a possible compromise in the test is identified, the test is ended, at 94.

Figure 7:
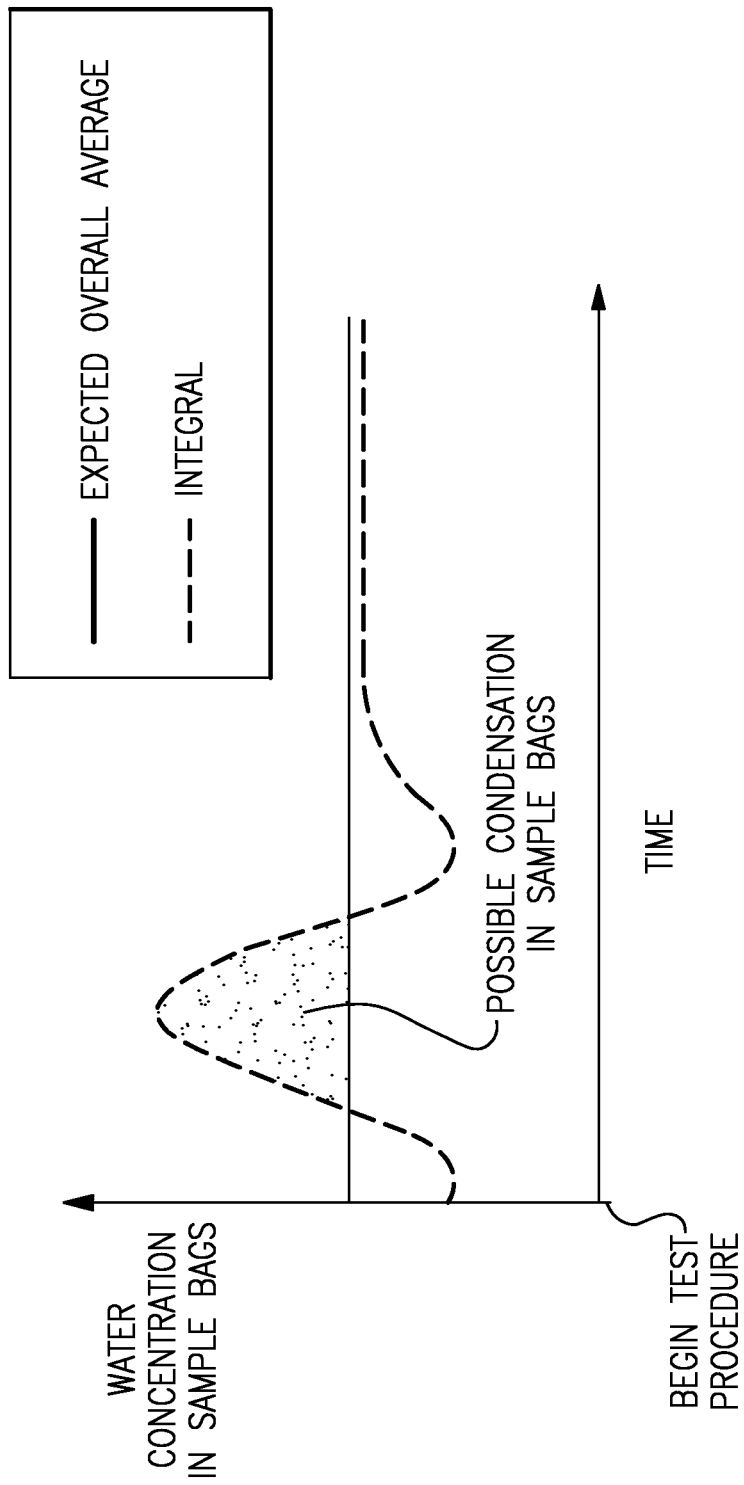
FIG. 7 is an example of the running average considered in the flow chart of FIG. 6.

FIG. 7 represents an example where a possible compromise occurs during the test procedure. In this example, $W_{bag-sat-int}$ exceeds an average $W_{bag-sat}$ expected over the test procedure, as illustrated in the shaded area. Thus, the bags may be over-saturated and condensation may be present.

This disclosure can be used to avoid condensation in more than just the sample bags of an exhaust system. As noted, there are several reasons to avoid condensation in more than just the sample bags, including more accurate testing, and compliance with new regulations.

This disclosure can be used to interrupt a compromised test procedure by monitoring for condensation during the test, rather than determining, after a completed test, that condensation had occurred. Interrupting a compromised test leads to time and cost savings relative to the alternative.

Although the different examples have the specific components shown in the illustrations, embodiments of this invention are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

What is claimed is:

1. An exhaust sampling system comprising:
    a plurality of exhaust sampling system zones, the exhaust sampling system zones including a sampling conduit, a fill circuit, a read circuit, and at least one sampling bag; and
    a controller programmed to:
        predict minimum dilution ratios to avoid condensation in each of the exhaust sampling system zones; and
        run a test procedure in which a sample of exhaust is diluted with make-up gas at a selected minimum dilution ratio that is greater than or equal to a maximum of the predicted minimum dilution ratios.

2. The system as recited in claim 1, wherein the selected minimum dilution ratio is equal to the maximum of the predicted minimum dilution ratios.

3. The system as recited in claim 1, wherein the selected minimum dilution ratio is within a range between 1:1 and 10:1.

4. A method of diluting an exhaust sample comprising:
    predicting, with a controller, minimum dilution ratios to avoid condensation in each of a fill circuit, a read circuit, a sampling conduit, and at least one sample bag; and
    diluting exhaust with a make-up gas, during a test procedure, at a ratio greater than or equal to a maximum of the predicted minimum dilution ratios.

5. The method as recited in claim 4, wherein the minimum dilution ratio to avoid condensation in the fill circuit $DR_{fill-min}$ is predicted in accordance with:

$$DR_{fill-min} \geq \frac{W_{ex-max}}{W_{fill-sat} - W_m}$$

where $W_{ex-max}$ is a maximum expected water concentration in the exhaust during the test procedure, $W_{fill-sat}$ is an expected saturated water concentration to be associated with the fill circuit during the test procedure, and $W_m$ is an expected water concentration in the make-up gas during the test procedure.

6. The method as recited in claim 4, wherein the minimum dilution ratio to avoid condensation in the read circuit $DR_{read-min}$ is predicted in accordance with:

$$DR_{read-min} \geq \frac{W_{ex-ave} - W_m}{W_{read-sat} - W_m}$$

where $W_{ex-ave}$ is an average expected water concentration in the exhaust during the test procedure, $W_{read-sat}$ is an expected saturated water concentration to be associated with the read circuit during the test procedure, and $W_m$ is an expected water concentration in the make-up gas during the test procedure.

7. The method as recited in claim 4, wherein the minimum dilution ratio to avoid condensation in the at least one sample bag $DR_{bag-min}$ is predicted in accordance with:

$$DR_{bag\text{-}min} \geq \frac{W_{ex\text{-}ave} - W_m}{W_{bag\text{-}sat} - W_m}$$

where $W_{ex\text{-}ave}$ is a maximum expected water concentration in the exhaust during the test procedure, $W_{bag\text{-}sat}$ is an expected saturated water concentration to be associated with the at least one sample bag during the test procedure, and $W_m$ is an expected water concentration in the make-up gas during the test procedure.

8. The method as recited in claim 4, wherein the minimum dilution ratio to avoid condensation in the sampling conduit $DR_{samp\text{-}cond\text{-}min}$ is predicted in accordance with:

$$DR_{samp\text{-}cond\text{-}min} \geq \frac{W_{ex\text{-}max} - W_m}{W_{samp\text{-}cond\text{-}sat} - W_m}$$

where $W_{ex\text{-}max}$ is a maximum expected water concentration in the exhaust during the test procedure, $W_{samp\text{-}cond\text{-}sat}$ is an expected saturated water concentration to be associated with the sampling conduit during the test procedure, and $W_m$ is an expected water concentration in the make-up gas during the test procedure.

9. The method as recited in claim 4, wherein the exhaust is diluted with the make-up gas at a minimum dilution ratio $DR_{CVS\text{-}MIN}$ that is determined based on the minimum dilution ratio to avoid condensation in the fill circuit $DR_{fill\text{-}min}$, the minimum dilution ratio to avoid condensation in the read circuit $DR_{read\text{-}min}$, the minimum dilution ratio to avoid condensation in the at least one sample bag $DR_{bag\text{-}min}$, and the minimum dilution ratio to avoid condensation in the sampling conduit $DR_{samp\text{-}cond\text{-}min}$ as follows:

$$DR_{CVS\text{-}MIN} \leq \max(DR_{fill\text{-}min}, DR_{read\text{-}min}, DR_{bag\text{-}min}, DR_{samp\text{-}cond\text{-}min}).$$

10. The method as recited in claim 9, wherein $DR_{CVS\text{-}MIN}$ is within a range between 1:1 and 10:1.

11. The method as recited in claim 4, wherein the exhaust is diluted with the make-up gas in the sampling conduit.

12. The method as recited in claim 4, wherein the exhaust is diluted with the make-up gas at a point downstream of the sampling conduit with a mini-diluter.

13. The method as recited in claim 4, further including predicting, with the controller, a minimum dilution ratio to avoid condensation in the sampling conduit.

14. The method as recited in claim 13, wherein the exhaust is diluted with the make-up gas at a maximum of the minimum dilution ratios predicted to avoid condensation in the sampling conduit, the fill circuit, the read circuit, and the at least one sample bag.

* * * * *

UNITED STATES PATENT AND TRADEMARK OFFICE
CERTIFICATE OF CORRECTION

PATENT NO. : 9,297,726 B2
APPLICATION NO. : 13/478170
DATED : March 29, 2016
INVENTOR(S) : William Martin Silvis et al.

Page 1 of 1

It is certified that error appears in the above-identified patent and that said Letters Patent is hereby corrected as shown below:

In the Claims

Column 10, Lines 9-10 (Claim 9),

"$DR_{CVS-MIN} \leq \max(DR_{fill-min}, DR_{read-min}, DR_{bag-min}, DR_{samp-cond-min})$" should be --$DR_{CVS-MIN} \geq \max(DR_{fill-min}, DR_{read-min}, DR_{bag-min}, DR_{samp-cond-min})$--.

Signed and Sealed this
Seventh Day of June, 2016

Michelle K. Lee
*Director of the United States Patent and Trademark Office*